United States Patent
Meng et al.

(10) Patent No.: US 6,844,287 B2
(45) Date of Patent: Jan. 18, 2005

(54) SUPPORTED CATALYSTS FOR THE FIXATION OF CARBON DIOXIDE INTO ALIPHATIC POLYCARBONATES AND A PROCESS FOR PREPARING THE SAME

(75) Inventors: Yuezhong Meng, Guangzhou (CN); Quan Zhu, Guangzhou (CN); Shizhen Zhang, Guangzhou (CN); Xiuhua Li, Guangzhou (CN); Longchao Du, Guangzhou (CN)

(73) Assignee: Guangzhou Institute of Chemistry, Chinese Academy of Sciences, Guangzhou (CN)

( * ) Notice: Subject to any disclaimer, the term of this patent is extended or adjusted under 35 U.S.C. 154(b) by 97 days.

(21) Appl. No.: 10/319,442

(22) Filed: Dec. 13, 2002

(65) Prior Publication Data

US 2003/0134740 A1 Jul. 17, 2003

(30) Foreign Application Priority Data

Dec. 18, 2001 (CN) ........................................ 01130099 A

(51) Int. Cl.[7] ................................................ B01J 31/00
(52) U.S. Cl. ........................ 502/150; 502/151; 502/170; 558/260; 558/277; 525/453; 525/394; 528/405
(58) Field of Search ................................. 502/150, 151, 502/170; 558/260, 277; 525/453, 394; 528/405

(56) References Cited

U.S. PATENT DOCUMENTS

| 4,079,038 A | * | 3/1978 | Choi et al. ..................... 528/86 |
| 4,325,874 A | * | 4/1982 | Jacobson ..................... 549/230 |
| 4,789,727 A | * | 12/1988 | Sun ............................. 528/405 |
| 4,824,969 A | * | 4/1989 | Austin et al. ................ 549/230 |
| 4,861,909 A | * | 8/1989 | Harris ........................ 558/267 |
| 4,943,677 A | * | 7/1990 | Rokicki ...................... 528/405 |
| 4,948,862 A | * | 8/1990 | Harris .......................... 528/77 |
| 4,960,862 A | * | 10/1990 | Carroll et al. .............. 528/405 |
| 5,084,528 A | * | 1/1992 | Harris ........................ 525/453 |
| 5,349,077 A | * | 9/1994 | Doya et al. ................. 558/260 |
| 5,498,743 A | * | 3/1996 | Shih et al. .................. 558/277 |
| 6,407,279 B1 | * | 6/2002 | Buchanan et al. .......... 558/277 |

* cited by examiner

*Primary Examiner*—Mark L. Bell
*Assistant Examiner*—Jennine M Brown
(74) *Attorney, Agent, or Firm*—Kinney & Lange, PA

(57) ABSTRACT

The present invention provides a process for preparing supported zinc dicarboxylate catalysts with high activity for the copolymerization of carbon dioxide and epoxides by supporting zinc dicarboxylate on silica support. The zinc dicarboxylate may be synthesized from zinc oxide and dicarboxylic acid such as succinic acid, glutaric acid, adipic acid, pimelic acid and suberic acid. The silica support can be selected from the group consisting of aerosil, silica gel for chromatography or reagent grade silicon dioxide. The supporting process is performed in a planetary ball grinder under vacuum.

7 Claims, No Drawings

SUPPORTED CATALYSTS FOR THE FIXATION OF CARBON DIOXIDE INTO ALIPHATIC POLYCARBONATES AND A PROCESS FOR PREPARING THE SAME

TECHNICAL FIELD OF THE INVENTION

The present invention relates to a supported catalyst with high activityuseful in the synthesis of poly(alkylene carbonate) polymers derived from the copolymerization of carbon dioxide and epoxides, a method for preparing the same.

BACKGROUND OF THE INVENTION

Carbon dioxide ($CO_2$) is currently considered as a major environmental pollutant that causes a dramatic increase in the global temperature or the so-called greenhouse effect. The contribution of $CO_2$ to the climate warming is estimated to be about 66%. The $CO_2$ level in atmosphere is now reported to be about 345 ppmv (parts per million by volume), and annually increases at a rate of about 1 ppmv due to human activities, especially in the case of using mineral fuel. Thus, the reduction of massive $CO_2$ release into the atmosphere has attracted much attention of the scientists all over the world. In this regard, the use of $CO_2$ as a polymerization monomer is of practical important. Aliphatic polycarbonates or the block copolymers of polycarbonate and polyether can be prepared via the direct copolymerization of $CO_2$ with epoxides such as ethylene oxide (EO), propylene oxide (PO), isobutylene oxide (BO), and cyclohexene oxide (CHO). The copolymerization of carbon dioxide with epoxides to form poly(alkylene carbonate) polymers was first reported by Inoue and co-workers, *Polymer Letters* 7, 287(1969); *Makromol. Chem.* 130.210(1969); and described in U.S. Pat. No. 3,585,168. Other processes are described in U.S. Pat. Nos. 3,900,424; 3,953,383 and 5,026,676. However, the progress for the commercialization of these poly(alkylene carbonate)s that utilize this chemistry has been very slow, although there are numerous economic advantages associated with the use of an abundant, low cost material like carbon dioxide. The main reason lies with the practical difficulty in preparing large scale organometallic catalysts for commercial usage.

The catalysts reported by Inoue were prepared by reacting diethylzinc with compounds containing active protons, e.g., water, dicarboxylic acids, or dihydric phenols. Typical catalyst productivities ranged from 2.0 to 10.0 grams of polymer per gram of catalyst used, and most of the yields fall at the low end of this range. Long polymerization time periods of 24 to 48 hours were required in order to achieve satisfactory yields and higher molecular weights of the products. It should be noted that the inoue catalysts also generated noticeable amounts of byproducts of cyclic carbonate and polyether homopolymer that must be removed from the desired polycarbonate polymers.

Zinc carboxylates have also been described as effective catalysts for $CO_2$ polymerization. Because zinc carboxylates are stable and safe compounds having no handling problem when comparing with diethylzinc, they are promising candidates for use as practical commercial catalyst systems. Soga and co-workers, *Polymer J.* 13(4), 407(1981) reported that the reaction products of zinc hydroxide and aliphatic dicarboxylic acids exhibited high activity for the copolymerization of carbon dioxide and propylene oxide. A variety of acids were tested, but only adipic and glutaric acid produced catalysts with higher activity than the known diethylzinc catalysts. Catalysts prepared from aromatic dicarboxylic acids were essentially inert under the polymerization conditions described by Soga.

Soga, *Nippon Kagakkaishi* 2, 295(1982) also reported another approach to improve the catalyst activity via supporting the catalyst on an inert Oxide Carrier. A supporting material can increase the surface area of active catalyst material, thereby enhancing the efficiency production of the aliphatic polycarbonate. In Soga's work, zinc acetate was selected as catalytically active component, and dissolved in some solvent, e.g. ethanol, to form a solution. After the silica support being added, the solvent is removed to give a supported catalyst. However, thus obtained catalyst has low activity due to the poor catalytic efficiency of zinc acetate. The supported catalysts of Soga are ineffective compared to the well-known diethylzinc based catalysts.

The metal salts of acetic acid are the third type of catalyst materials known to promote the copolymerization of $CO_2$ with epoxides (Soga. et al., *Makromol. Chem.* 178, 893 (1977)). Only zinc and cobalt can produce alternating copolymers from $CO_2$ and epoxides, and the activity of these catalysts is lower than that derived from diethylzinc based catalysts.

In U.S. Pat. No. 4,783,445, Sun reported that soluble zinc catalysts can be prepared by reacting zinc oxide or zinc salts with a dicarboxylic acid anhydride or monoester in a suitable solvent such as the lower alcohols, ketones, esters and ethers. However, low catalytic activity is produced.

Among the catalyst systems reported in the literature up to that time, only zinc carboxylates based on adipic or glutaric acid seem potential for practical use on a commercial scale.

DISCLOSURES OF THE INVENTION

One object of the present invention is to provide a process for preparing supported catalysts useful in the copolymerization of carbon dioxide and epoxides to form poly (alkylene carbonate)s, comprising the step of supporting a zinc dicarboxylate on the silica support, wherein the zinc dicarboxylate is selected from the group consisting of zinc succinate, zinc glutarate, zinc adipate, zinc pimelate and zinc suberate, and the mixture thereof, and the weight ratio of zinc dicarboxylate to silica support varies from 1/1 to 1/15.

An another object of the present invention is to provide a supported catalyst useful in the copolymerization of carbon dioxide and epoxides to form poly(alkylene carbonate)s, obtained by abovementioned process.

This invention provides a new procedure for the preparation of supported catalysts containing zinc dicarboxylate used for the preparation of copolymers of epoxide materials and carbon dioxide. The zinc dicarboxylates may be synthesized from zinc oxide and dicarboxylic acid by conventional method known in the art. Said dicarboxylic acid may be selected from the group consisting of succinic acid, glutaric acid, adipic acid, pimelic acid, suberic acid, and the mixture thereof. The zinc dicarboxylate is preferably zinc glutarate, zinc adipate and zinc pimelate.

The silica support suitable for the present invention may come from various sources. The examples of suitable the silica support include, but not limited to, aerosil, silica gel for chromatography or reagent grade silicon dioxide. For the aerosil, the average particle size of silica support may be from about 200 nm to about 300 nm. Said silica support can be activated by calcining at a temperature of from about 200° C. to about 1100° C., preferably from about 400° C. to about 1000° C., more preferably from about 500 to about 900° C., and most preferably from about 600° C. to about 800° C. in a muffle furnace or tubular furnace for about 30 minutes to 48 hours, preferably about 1 to about 24 hours, more preferably about 2 to about 16 hours prior to usage. Upon activated, the support is preferably kept without further contacting with any moisture.

The supporting process may be performed in a planetary ball grinder. In a vacuum agate tank, zinc dicarboxylate and silica support are milled by a planetary ball grinder with a revolutions scale from about 200 to 500 per minute for about 10 minutes to 12 hours, preferably about 20 minutes to 6 hours, and more preferably about 30 minutes to 2 hours.

In the supported catalyst, the weight ratio of zinc dicarboxylate to silica support may be from about 1/1 to about 1/15, preferably about 1/2 to about 1/5.

The supported catalysts can be used in the copolymerization of $CO_2$ and PO. Experimental results show that extremely high catalytic efficiency can be achieved. Without limited to a specific theory, it is believed that the increase of the activity is contributed by the increase of the specific surface area of the particles of zinc dicarboxylate achieved by atomizing and distributing the particles of zinc dicarboxylate on silica support by means of machinary grinding. In addition, the silica support have moisture absorption ability such that it can be utilized for absorbing trace of moisture presenting in the carbon dioxide and epioxides feed, thereby increasing further the catalytic efficiency and molecular weight of the polymer product.

The catalyst obtainable in the present invention process is white powder, and stable in dry air. Said catalyst is hygroscopic in some extent, but its activity can be restored by activating by means of heat-dehydrating.

The supported catalysts derived from zinc glutarate and zinc pimelate have an advantage of high activity, and that derived from zinc adipate has an advantage of low cost.

A more detailed description of the invention and its methods of practice are described in the following examples. It should be understood that the present invention is not intended to limit into these examples in any way.

EXAMPLE

General Procedure
Pretreatment of Materials

Epoxide, e.g., propylene oxide (PO) with a purity of 99.5% was purified by distillation over calcium hydride under dry nitrogen atmosphere for 2 hours. The as-treated PO was then stored over 4A molecular sieves prior to use. Carbon dioxide with a purity of higher than 99.8% was used as received. Dicarboxylic acid of 98.0% purity, and solvents such as toluene, methanol, acetone, methylene dichloride, were of analytical reagent grade and used without further purification. Zinc oxides of 99.99% purity were also used without further treatment. The silica supports were activated under 700–800° C. in a muffle furnace for 10–16 hours.

Preparation of Zinc Dicarboxylates

Zinc dicarboxylates were synthesized from zinc oxide and dicarboxylic acid under magnetic stirring as described in the literature. Fine powders of zinc oxide were used as received without further grinding. Accordingly, to a 150 mL three-neck round bottom flask equipped with a magnetic stirrer, condenser, and a Dean-Stark trap were added a slight molar excess zinc oxide and 90 mL toluene. To this mixture was then introduced dicarboxylic acid, and the mixture was slowly heated up to 55–110° C. for 4 to 20 hours under vigorous stirring. Upon cooling, the resulting mixture was filtered. The resulting solids were continuously washed with acetone for several times followed by drying overnight in a vacuum oven at 100° C. The obtained zinc dicarboxylates was fine powders in white color with a high acid conversion.

Preparation of Supported Catalysts

The silica support were selected from the group consisting of aerosil, silica gel for chromatography and reagent grade silicon dioxide. They were activated under 700–800° C. in a muffle furnace for 10–16 hours prior to usage. In a vacuum agate tank, zinc dicarboxylate and silica support (weight ratio from 1/1 to 1/15) were milled by a planetary ball grinder with a revolutions scale from 200 to 500 per minute for 30 to 120 minutes. The supported catalyst was obtained accordingly.

Copolymerization

The copolymerization of $CO_2$ and epoxides, e.g. propylene oxide was carried out in a 500 mL autoclave equipped with a mechanical stirrer. Supported catalyst was further dried at 100° C. for 24 hours prior to being used for the polymerization process. Dry supported catalyst was then introduced into the autoclave as quickly as possible. The autoclave was then capped with its head, and the entire assembly was connected to the reaction system equipped with a vacuum line. The autoclave with catalyst inside was further dried for 24 h under vacuum at 100° C. This implied that the catalyst was further in-situ dried during the same process for another 24 hours. Subsequently, the autoclave was purged with carbon dioxide and evacuated alternatively for three times, followed by adding purified PO with a syringe. The autoclave was then pressurized to 5.0 MPa via a $CO_2$ cylinder. The copolymerization was performed at 60° C. under stirring for 40 hours. The autoclave was cooled to room temperature and the pressure was released. The resulting viscous mixture was removed, dissolved in a proper volume of methylene chloride and transferred to a separating funnel. The catalyst residual was extracted from the product solution by using 200 ml dilute hydrochloric acid (5%), followed by washing three times with distilled water. The viscous solution was concentrated by using a rotary evaporator to give a proper concentration. Finally, poly(propylene carbonate) copolymer was precipitated out by pouring the concentrated copolymer solution into vigorously stirred methanol. The as-made PPC was filtered and dried for two days at room temperature under vacuum. Meanwhile, the resulting filtrate was distilled to remove methanol and methylene chloride to yield a methanol soluble product.

Examples 1–8

Zinc dicarboxylates were synthesized in examples 1–8. The preparation condition and result were listed in Table 1. In each example satisfactory conversion of acid was achieved.

TABLE 1

Preparation of zinc dicarboxylates

| Example No. | Dicarboxylic acid | Acid/ZnO (mol/mol) | Reaction temperature(° C.) | Reaction time(hours) | Conversion of acid(%) |
|---|---|---|---|---|---|
| 1 | Succinic acid | 0.98 | 60 | 10 | 95.4 |
| 2 | Glutaric acid | 0.98 | 55 | 10 | 99.78 |
| 3 | Glutaric acid | 0.98 | 60 | 20 | 99.48 |
| 4 | Glutaric acid | 0.98 | 90 | 8 | 97.66 |
| 5 | Adipic acid | 0.96 | 80 | 10 | 99.42 |
| 6 | Adipic acid | 0.96 | 80 | 20 | 98.94 |
| 7 | Pimelic acid | 0.98 | 60 | 10 | 99.22 |
| 8 | Suberic acid | 0.96 | 80 | 12 | 95.20 |

Examples 9–13

In examples 9–13, zinc dicarboxylates obtained from the examples 1, 2, 6, 7, 8 were supported on the silica support respectively. The supporting condition was listed in Table 2. The as-made supported catalysts were used in the copolymerization of $CO_2$ and PO and catalytic activity results were also listed in Table 2. From Table 2, it can be seen that extremely high catalytic activity can be achieved by using either supported zinc glutarate, supported zinc adipate or supported zinc pimelate. The catalytic activity of zinc glutarate in example 10 (358.8 g polymer/g zinc) is nearly 1.9 times higher than that reported by M. Ree et al.

TABLE 2

Preparation and result of supported catalysts and poly(propylenecarbonate)

| Example No. | Zinc dicarboxylate | supporter | % | Supporting condition (rpm/min.) | Catalytic activity(g polymer/g zinc) |
|---|---|---|---|---|---|
| 9 | Zinc succinate | aerosil | 200 | 350/30 | 9.38 |
| 10 | Zinc glutarate | aerosil | 200 | 350/30 | 358.8 |
| 11 | Zinc adipate | aerosil | 200 | 350/30 | 234.9 |
| 12 | Zinc pimelate | Reagent grade silica | 300 | 250/60 | 325.4 |
| 13 | Zinc suberate | silica gel for chromatography | 300 | 250/60 | 116.8 |
| ** | Zinc glutarate | — | — | — | 191.4 |

*copolymerization condition: 60 ° C., 40 hours, $CO_2$ pressure: 5.2 MPa
** M. Ree et al., "A new copolymerization process leading to poly (propylenecarbonate) with a highly enhanced yield from carbon dioxide and propylene oxide", Journal of Polymer Science: Part A: Polymer Chemistry, 37,1863–1876(1999).

We claim:

1. A process for preparing supported catalysts for the copolymerization of carbon dioxide and epoxides to form poly(alkylene carbonate)s, comprising the step of supporting a zinc dicarboxylate on silica, wherein the zinc dicarboxylate is selected from the group consisting of zinc succinate, zinc glutarate, zinc adipate, zinc pimelate and zinc suberate, and the mixture thereof, and the weight ratio of zinc dicarboxylate to silica support varies from 1/2 to 1/5.

2. The process of claim 1, wherein said zinc dicarboxylate is selected from the group consisting of zinc glutarate, zinc adipate and zinc pimelate.

3. The process of claim 1, wherein the silica support is selected from the group consisting of aerosil, silica gel for chromatography and reagent grade silicon dioxide.

4. The process of claim 3, wherein said silica support is aerosil or silica gel.

5. The process of claim 1, wherein said supporting process is carried out in a planetary ball grinder under vacuum, and the silica support may be activated prior to usage.

6. The process of claim 5, wherein said supporting process is performed at the revolutions ranging from 200 to 500 per minute for 30 to 120 minutes.

7. A supported catalyst for the copolymerization of carbon dioxide and epoxides to form poly(alkylene carbonate)s obtained by supporting a zinc dicarboxylate on silica, wherein the zinc dicarboxylate is selected from the group consisting of zinc succinate, zinc glutarate, zinc adipate, zinc pimelate and zinc suberate, and the mixture thereof, and the weight ratio of zinc dicarboxylate to silica support varies from 1/2 to 1/5.

* * * * *